United States Patent [19]

Tominaga

[11] Patent Number: 5,747,049
[45] Date of Patent: May 5, 1998

[54] COSMETIC COMPOSITION

[75] Inventor: Naoki Tominaga, Kanagawa, Japan

[73] Assignees: Shiseido Company, Ltd.; Sogo Pharmaceutical Co. Ltd., both of Tokyo, Japan

[21] Appl. No.: 529,601

[22] Filed: Sep. 18, 1995

[30] Foreign Application Priority Data

Jul. 7, 1995 [JP] Japan .................................. 7-195965

[51] Int. Cl.$^6$ .................................................. A61K 7/48
[52] U.S. Cl. ........................... 424/401; 424/59; 514/844; 514/846
[58] Field of Search ..................... 424/401, 59; 514/844, 514/846

[56] References Cited

FOREIGN PATENT DOCUMENTS

| 0 222 313 | 5/1987 | European Pat. Off. . |
| 0 370 994 | 5/1990 | European Pat. Off. . |
| 0 506 961 | 10/1992 | European Pat. Off. . |
| 42 44 090 | 8/1993 | Germany . |
| 7-233046 | 9/1995 | Japan . |
| 86/00014 | 1/1986 | WIPO . |
| 90/06102 | 6/1990 | WIPO . |

OTHER PUBLICATIONS

Fujimoto, "Cross-Linking of Collagen", Cutaneous Aging, Edited by Albert Kligman and Yoshio Takase, University of Tokyo Press, 1988, pp. 263–274.

Sugiyama et al. "Relationship Between the age and Histidinoalanine Content of Human Aorta". Biomedical Research, vol. 8, No. 5, 1987, pp. 349–351.

Fujimori, Cross-Linking of Collagen CNBr Peptides by Ozone or UV Light, Federation of European Biochemical Societies, vol. 235, No. 1,2, pp. 98–102, Aug. 1988.

Patent Abstracts of Japan, vol. 10, No. 235 (C-366), Aug. 14, 1986 & JP-A-61 069707 (Sogo Yatsukou KK) Apr. 10, 1986.

Patent Abstracts of Japan, vol. 4, No. 562 (C-788), Dec. 13, 1990 & JP-A-02 243647 (Pias Arise KK), Sep. 27, 1990.

Patent Abstracts of Japan, vol. 11, No. 80 (C-409), Mar. 11, 1987 & JP-A-61 236707 (Shiseido Co. Ltd.) Oct. 22, 1986.

Database WPI, Week 9423, Derwent Publications Ltd., London, GB; AN 94-186353 & JP-A-06 122 618 (Shiseido Co. Ltd.), May 6, 1994.

Blaisdell, et al. "Dietary Supplementation with Taurine and Niacin Prevents the Increase in Lung Collagen cross-links", Chemical Abstracts of Japan, vol. 121, No. 11, Sep. 1994, Columbus, Ohio, US:Abstract No. 132860, p. 912, col. 4.

Database WPI, Week 8749, Derwent Publications Ltd., London, GB; AN 87-345514 & JP-A-62 249 908 (Lion Corp.), Oct. 30, 1987.

Patent Abstracts of Japan, vol. 10, No. 31 (C-327), Feb. 6, 1986 & JP-A-60 185708 (Shiseido KK) Sep. 21, 1985.

*Primary Examiner*—Jyothsan Venkat
*Attorney, Agent, or Firm*—Cushman Darby & Cushman IP Group of Pillsbury Madison & Sutro LLP

[57] ABSTRACT

An anti-aging preparation for cutaneous application which prevents cutaneous aging, a collagen cross-linking inhibitory preparation for cutaneous application which inhibits collagen cross-linking occurring predominantly in the dermis to maintain skin elasticity and to prevent wrinkles or sagging, and an anti-UV preparation for cutaneous application which protects the skin from harmful effects caused by of excessive exposure to ultraviolet rays of sunlight are disclosed. The preparation contains one or two aminoethyl compounds represented by formula (I):

$$NH_2CH_2CH_2X \qquad (I)$$

wherein X represents $-SO_2H$ or $-SO_2SH$, and preferably contains at least one ultraviolet protective agent.

21 Claims, No Drawings

COSMETIC COMPOSITION

FIELD OF THE INVENTION

This invention relates to an anti-aging preparation for external application to the skin which inhibits cutaneous aging, a collagen cross-linking inhibitory preparation for external application to the skin which inhibits collagen cross-linking occurring predominantly in the dermis to maintain skin elasticity and to suppress wrinkles or sagging, and an anti-ultraviolet preparation for external application to the skin which protects the skin from harmful effects caused by of excessive exposure to ultraviolet light.

BACKGROUND OF THE INVENTION

It is known that skin gets thinner and reduces its metabolism with aging.

While advancing years are a macroscopically significant factor causing cutaneous aging, influences of dryness, oxidation, and ultraviolet (UV) rays of sunlight are believed to be causes which directly attribute to cutaneous aging.

Various means for inhibiting the skin from being aged have hitherto been taken. For example, (1) preparations for external use containing various humectants for inhibiting cutaneous aging caused by dryness, (2) preparations for external use containing antioxidants for inhibiting cutaneous aging caused by oxidation, such as vitamin E, and (3) preparations for external use containing ultraviolet absorbers for inhibiting cutaneous aging caused by exposure to UV light have been proposed.

However, all these means conventionally taken for prevention of cutaneous aging are based on efforts to minimize the above-mentioned external factors which, as a result, relate to cutaneous aging and are no better than a kind of symptomatic treatment. There is no denying that the effects produced are insufficient. Hence, it has been demanded to establish a means of radical treatment for stopping or inhibiting a phenomenon which accelerates cutaneous aging more directly.

Increase of collagen cross-linking mainly in the dermis is known as a phenomenon which accelerates cutaneous aging more directly (see Albert M. Kligman and Yoshio Takasu (ed.), *Cutaneous Aging*, pp. 263–274, University of Tokyo Pres. (1988) and Sugiyama T.; Fujimoto D., Arai C. and Hasegawa M., *Biomed. Res.*, Vol. 8, pp. 349–351 (1987)).

That is, the above-mentioned factors of cutaneous aging, especially exposure to long-wavelength UV rays (hereinafter referred to as UV-A) easily reaching to the dermis, are accompanied by reductions in growth activity of fibroblasts which are main cells in the dermis or functions of metabolic turnover (synthesis and decomposition) of collagen, etc., and thereby reduction in turnover rate of collagen, etc. With respect to UV-induced collagen cross-linking, reference can be made in Fujimori E., *FEBS Lett.*, Vol. 235 (1–2), pp. 98–102 (1988). It seems to follow that collagen, etc. undergo various modifications or denaturation, resulting in increased cross-linking of collagen in the skin.

As collagen cross-linking proceeds, the skin loses its elasticity, and wrinkles and sagging increase, and cutaneous aging thus proceeds.

SUMMARY OF THE INVENTION

An object of the present invention is to establish a radical treatment for stopping the progress of collagen cross-linking and to provide preparations for external application to the skin which would meet various demands in industry, such as prevention of cutaneous aging.

As a result of extensive investigations, the inventors of the present invention have found that specific aminoethyl compounds have an effect on suppression of collagen cross-linking and that the above object of the present invention is accomplished by using these compounds either singly or in combination with an ultraviolet light protective agent as an active ingredient(s).

The present invention provides:

(1) an anti-aging preparation for external application to the skin containing one or two of aminoethyl compounds represented by formula (I):

$$NH_2CH_2CH_2X \qquad (I)$$

wherein X represents —$SO_2H$ or —$SO_2SH$;

(2) an anti-aging preparation for external application to the skin according to (1) above, wherein the preparation further contains at least one UV protective agent;

(3) an anti-aging preparation for external application to the skin according to (2) above, wherein the UV protective agent comprises at least one UV-A protective agent;

(4) an anti-aging preparation for external application to the skin according to (3) above, wherein the UV-A protective agent is 4-methoxy-4'-t-butyldibenzoylmethane, 2-hydroxy-4-methoxybenzophenone and/or a 2-hydroxy-4-methoxybenzophenone derivative;

(5) an anti-aging preparation for external application to the skin according to any one of (1) to (4) above, wherein the aminoethyl compound(s) (I) is/are present in a total amount of from 0.001 to 1.0% by weight based on the total preparation;

(6) an anti-aging preparation for external application to the skin according to any one of (1) to (4) above, wherein the aminoethyl compound(s) (I) is/are present in a total amount of from 0.01 to 0.5% by weight based on the total preparation;

(7) an anti-aging preparation for external application to the skin according to any one of (2) to (6) above, wherein the UV protective agent is present in a total amount of from 0.01 to 30% by weight based on the total preparation;

(8) an anti-aging preparation for external application to the skin according to any one of (2) to (6) above, wherein the UV protective agent is present in a total amount of from 0.1 to 20% by weight based on the total preparation;

(9) an anti-aging preparation for external application to the skin according to any one of (1) to (8), wherein the anti-aging preparation is a collagen cross-linking inhibitory preparation; and

(10) an anti-aging preparation for external application to the skin according to any one of (1) to (8), wherein the anti-aging preparation is an anti-UV preparation.

DETAILED DESCRIPTION OF THE INVENTION

The anti-aging preparation for external application to the skin, collagen cross-linking inhibitory preparation for external application to the skin, and anti-ultraviolet preparation for external application to the skin (hereinafter inclusively referred to as preparations for cutaneous application) according to the present invention contain an aminoethyl compound represented by formula (I).

Both the aminoethyl compound of formula (I) wherein X is a sulfinic acid group (—$SO_2H$), i.e., 2-aminoethylsulfinic acid (Hypotaurine), and the aminoethyl compound of formula (I) wherein X is a thiosulfonic acid group (—$SO_2SH$), i.e., 2-aminoethylthiosulfonic acid (Thiotaurine), are present in main organs of many mammals including humans, such as the heart, the brain and the liver, and also contained in quantity in daily foods. No side effects of these compounds on the skin, such as irritation, itching and eruption, have been reported.

It is obvious therefore that incorporation of the aminoethyl compounds of formula (I) into preparations for cutaneous application as in the present invention incurs no problem.

The aminoethyl compounds (I) can easily be prepared from easily available thio compounds, e.g., cysteine, in a usual known manner. Commercially available compounds of formula.(I) may also be used.

When incorporated into preparations for cutaneous application, the aminoethyl compounds (I) exhibits inhibitory action on collagen cross-linking thereby making a great contribution to manifestation of the effects expected of the preparations.

That is, the collagen cross-linking inhibitory preparation of the present invention inhibits collagen cross-linking to make it possible to retain skin elasticity, suppress the development of wrinkles or sagging and maintain a beautiful skin as far as collagen cross-linking is concerned.

The UV protective preparation of the present invention makes it possible to suppress photo-aging of the skin due to UV-A-induced collagen cross-linking thereby protecting the skin against the harmful effects of UV on the skin.

Further, the anti-aging preparation of the present invention is effective to suppress diminishment of skin elasticity, generation of wrinkles, and skin sagging due to cutaneous aging caused by not only the above-mentioned photo-aging, but also advancing years.

The amount of the aminoethyl compound (I) to be incorporated into the preparations is subject to variation depending on the purpose of the preparation and the kinds and amounts of other ingredients present in the preparation, but generally ranges from 0.001 to 1.0% by weight based on the total preparation. If the amount of compound (I) is less than 0.001% by weight, it is difficult to make use of the collagen cross-linking inhibitory activity in practice to produce the above-mentioned specific effects as expected. On the other hand, increasing the amount of the compound (I) to exceed 1.0% by weight is not accompanied by further enhancement of the effects in collagen cross-linking inhibitory activity.

Taking into consideration the balance between the intensity of the effects exhibited and the amount of the compound incorporated, a preferred amount of the aminoethyl compound (I) to be incorporated ranges from 0.01 to 0.5% by weight based on the total preparation.

If the amount of the aminoethyl compound (I) is 0.001% by weight or more but is less than 0.01% by weight, the collagen cross-linking inhibitory effect produced by the compound alone is often insufficient and, as a result, it tends to be necessary to increase the amounts of other auxiliary ingredients.

If the amount of the aminoethyl compound (I) is 1.0% by weight or less but exceeds 0.5% by weight, the rate of enhancement of the desired effects vs. the increase in amount of the compound would be small, and in some instances the collagen cross-linking inhibitory effects are enhanced by positively adding other auxiliary ingredients rather than increasing the amount of the aminoethyl compound.

The above-mentioned two aminoethyl compounds (I) may be used either individually or as a combination thereof. There is a tendency that the combined use of the two compounds (I) produces enhanced collagen cross-linking inhibitory activity as compared with individual use. The ratio of the two compounds (I) when used in combination is arbitrary and is not particularly limited.

The preparations for cutaneous application according to the present invention may further contain a UV protective agent. The term "UV protective agent" as used herein denotes both a "UV absorber" which absorbs ultraviolet light physicochemically and a "UV screening agent" which scatters and reflects ultraviolet light physicochemically.

Incorporation of a UV protective agent into the preparation of the present invention makes the preparation produce the desired effects synergistically. That is, the quantity of UV light reaching the skin is reduced to synergistically hinder collagen cross-linking, thereby further enhancing the effects of maintaining skin elasticity and suppressing wrinkles or sagging. There is thus provided a collagen cross-linking inhibitory preparation which is more effective for maintaining a beautiful skin.

Besides the synergistic inhibitory effect on collagen cross-linking owing to the reduction in UV light quantity reaching the skin, incorporation of a UV protective agent is effective to diminish various harmful effects of UV light upon a human body other than acceleration of collagen cross-linking. In other words, a combined use of a UV protective agent and the aminoethyl compound (I) in preparations for cutaneous application controls the particular serious phenomenon, i.e., acceleration of collagen cross-linking by exposing UV light, to thereby provide an anti-UV preparation for cutaneous application producing higher UV-resistant effects than an anti-UV preparation containing a UV protective agent as a sole active ingredient.

Incorporation of a UV protective agent into the preparation of the present invention makes it possible not only to effectively control collagen cross-linking which steadily proceeds with advancing cutaneous age but also to suppress other actions of UV light that would accelerate cutaneous aging, to thereby provide an anti-aging preparation for cutaneous application which is more effective for inhibiting the progress of cutaneous aging.

The UV screening agent which can be used in the present invention is not particularly limited as long as it can be incorporated physicochemically into the preparation of the present invention and is capable of producing the above-described synergistic effects when incorporated into the preparation. Examples of suitable UV protective agents are shown below for illustrative purposes only, and should not be construed as limiting.

UV-A absorbers include anthranilic acid derivatives, such as methyl anthranilate and homomentyl N-acetylanthranilate; benzophenone derivatives, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salts, 4-phenylbenzophenone, 2-ethylhexyl-4'-phenylbenzophenone-2-carboxylates, 2-hydroxy-4-n-octoxybenzophenone, and 4-hydroxy-3- carboxybenzophenone; benzotriazole derivatives, such as 2,2'-hydroxy-5-methylphenylbenzotriazole, 2-(2'-hydroxy-5'-t-octylphenyl)benzotriazole and 2-(2'-hydroxy-5'-methylphenyl)benzotriazole; dianisoylmethane, and 4-methoxy-4'-t-butyldibenzoylmethane (Parsol A™). Preferred of these UV-A absorbers are 4-methoxy-4'-t-butyldibenzoylmethane, 2-hydroxy-4-methoxybenzophenone, and 2-hydroxy-4-methoxybenzophenone derivatives, e.g., 2-hydroxy-4-methoxybenzophenone-5-sulfonic acid salts, for their safety and efficacy.

Medium-wavelength ultraviolet (hereinafter referred to as UV-B) absorbers include benzoic acid derivatives, such as p-aminobenzoic acid (hereinafter abbreviated as PABA), glycerol mono-PABA ester, N,N-dipropoxyPABA ethyl ester, N, N-diethoxyPABA ethyl ester, N,N-dimethylPABA ethyl ester, N, N-dimethylPABA butyl ester, and N,N-dimethylPABA amyl ester; salicylic acid derivatives, such as dipropylene glycol salicylate, ethylene glycol salicylate, myristyl salicylate, methyl salicylate, amyl salicylate, mentyl salicylate, homomentyl salicylate, octyl salicylate, phenyl salicylate, benzyl salicylate, and p-isopropylphenyl salicylate; cinnamic acid derivatives, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glycerol mono-2-ethylhexanoyl-di-p-methoxycinnamate, octyl methoxycinnamate, 3-methyl-4-[methylbis(trimethylsiloxy)silyl]butyl 3,4,5-trimethoxycinnamate, and monoethyl p-dimethoxycinnamate; camphor derivatives, such as 3-(4'-methylbenzylidene)-d, l-camphor, 3-benzylidene-d,l-camphor, and 5-(3,3-dimethyl-2-norbornylidene)-3-pentene-2-one; urocanic acid, ethyl urocanate, 2-phenyl-5-methylbenzoxazole, and dibenzalazine.

The UV screening agents include titanium oxide (TiO₂), talc (MgSiO₂), Carmine (FeO₂), bentonite, kaolin, and zinc oxide (ZnO).

These UV protective agents can be incorporated into the preparation of the present invention in an appropriate combination thereof in agreement with the particular purpose and form of the preparation. Collagen cross-linking is a phenomenon which occurs mainly in the dermal layer of the skin. Where a UV protective agent is used for the specific purpose of affecting synergistic inhibitory action on collagen cross-linking, it is recommended to select UV-A absorbers which absorb UV-A (wavelength: 320 to 400 nm) capable of reaching the dermal layer rather than UV-B absorbers which absorb UV-B (wavelength: 280 to 320 nm), it is particularly preferred in the present invention to positively use UV-A absorbers for the purpose of producing synergistic inhibitory effects on collagen cross-linking.

The denotation "UV-A absorbers" or "UV-B absorbers" as used herein does not always mean that the agents are capable of absorbing only UV-A or UV-B but means that they are capable of absorbing at least UV-A or UV-B. For example, the benzophenone UV absorbers mentioned above as examples of UV-A absorbers are capable of absorbing UV-B as well as UV-A.

The amount of the UV protective agent to be incorporated is subject to variation depending on the properties to be imparted to the preparation of the present invention. It is usually 0.01 to 30% by weight, preferably 0.1 to 20% by weight, based on the total preparation. If the amount is less than 0.01% by weight, the agent tends to fail to bring about synergistic effects that would have been obtained by addition of a sufficient amount of the agent. If the amount exceeds 30% by weight, any further enhancement of synergistic effects that might be expected from employing the increased amount hardly results.

The preparations for cutaneous application according to the present invention containing the above-described active ingredients are sufficiently expected to exhibit the respective effects as desired, i.e., inhibition of collagen cross-linking, inhibition of bad influences of UV light, and suppression of cutaneous aging.

If desired, to the extend that the effects of the present invention are not impaired, the preparations of the present invention may further contain other active ingredients added for imparting to the preparation those effects which are generally expected of preparations for cutaneous application.

For example, to impart a moisturizing effect to the preparation is effective for suppressing cutaneous aging caused by skin dryness. Examples of humectants which may be added to the preparation for imparting this moisturizing effect include polyethylene glycol, propylene glycol, glycerin, 1,3-butylene glycol, hexylene glycol, xylitol, sorbitol, maltitol, chondroitin sulfuric acid, hyaluronic acid, mucoitin sulfuric acid, caronic acid, Atelocollagen,-cholesteryl 12-hydroxystearate, sodium lactate, bile salts, dl-pyrrolidonecarboxylic acid salts, short chain soluble collagen, diglycerol (ethylene oxide) propylene oxide adduct, extract of chestnut rose, extract of malifoils (*Achillea millefolium*), and extract of melilots.

The inclusion of a whitening effect in the preparation is effective for alleviating the bad influences of UV light on the skin. To this effect, a whitening agent, such as placental extract, glutathione, extract of creeping saxifrage (*Saxifrage stolonifera*), etc. may be added to the preparation.

The provision of an antiinflammatory effect in the preparation is effective for alleviating the bad influences of UV light on the skin. To this effect, an antiinflammatory agent, such as a glycyrrhizic acid derivative, a glycyrrhetic acid derivative, a salicylic acid derivative, hinokitiol, zinc oxide, allantoin, etc. may be added to the preparation.

For the purpose of alleviating the bad influences of UV light on the skin and also suppressing cutaneous aging, the preparation of the present invention may further contain an activator, such as royal jelly, a photosensitizer, a cholesterol derivative, and fetal bovine blood extract; a blood flow accelerator, such as nonylic acid vanillylamide, benzyl nicotinate, β-butoxyethyl nicotinate, Capsaicin, Zingerone, Cantharides tincture, Ichthammol, caffeine, tannic acid, α-borneol, tocopherol nicotinate, inositol hexanicotinate, Cyclandelate, Cinnarizine, Tolazoline, acetylcholine, Verapamil, Cepharanthin, and γ-Oryzanol; and an antiseborrheic agent, such as sulfur and Thianthol.

It is also possible to add various plant extracts into the preparation for various purposes. Examples of usable plant extracts are phellodendron extract, coptis roots extract, Lithospermi radix extract, Paeoniae radix extract, Swertia extract, birch extract, sage extract, loquart extract, ginseng extract, aloe extract, common mallow extract, iris extract, grape extract, Coicis semen (*Coix lachryma-jobi*) extract (Yokuinin), loofah (*Luffa cylindrica Rosem*) extract, Lilium extract, crocus extract, Cnidii rhizoma extract, ginger extract, Saint-John's wort (*Hypericum erectum*) extract, petty white (*Ononis spinosa*) root extract, rosemary extract, garlic extract, capsicum extract, orange peel, and danguii (*Angelicae sinensis* (Oliv.) Diels).

Vitamins may also be added to the preparation in order to impart various peculiar effects to the preparation, for example, a cutaneous aging inhibitory effect. Examples of usable vitamins are vitamin A's, such as vitamin A oil, retinol, retinol acetate; vitamin $B_2$'s, such as riboflavin, riboflavin butyrate, and flavin adenine dinucleotide; vitamin $B_6$'s, such as pyridoxine hydrochloride and pyridoxine dioctanoate; vitamin C's, such as L-ascorbic acid, L-ascorbic acid palmitate, L-ascorbic acid 2-sulfate, L-ascorbic acid phosphate, and DL-α-tocopherol-L-ascorbic acid phosphate diester dipotassium; pantothenic acid derivatives, such as calcium pantothenate, D-pantothenyl alcohol, pantothenyl ethyl ether, and acetylpentothenyl ethyl ether; vitamin D's, such as ergocalciferol and cholecalciferol; nicotinic acid compounds, such as nicotinic acid, nicotinamide, and benzyl nicotinate; vitamin E's, such as α-tocopherol, tocopherol acetate, DL-α-tocopherol nicotinate, and DL-α-tocopherol succinate; and other vitamins such as vitamin P and biotin.

The active ingredients which may be incorporated into the preparation of the present invention are not limited to the above-enumerated specific examples. Further, the pharmacological efficacy of the above-enumerated active ingredients is not limited to the one described. For example, vitamin C's are useful as not only a whitening agent but an antioxidation assistant. These active ingredients may be incorporated into the preparation either individually or as an appropriate combination of two or more thereof according to the purpose prescribed for the preparation.

The present invention is broadly applicable to cosmetics, pharmaceuticals and non-medical applications which are externally applied to the skin and may take a wide variety of forms, such as aqueous solutions, solubilized systems, emulsions, powders, oily liquids, gels, ointments, aerosols, water-oil two phase systems, water-oil-powder three phase systems, and the like. For example, the preparations of the present invention are-applicable to a wide range of cosmetic forms, such as facial cleansers, clear lotions, milky lotions, creams, jellies, skin revitalizers, and facial packs as skin care cosmetics, and foundation creams as makeup cosmetics; and a wide range of pharmaceutical or non-medical application forms, such as ointments. The forms applicable to the preparations of the present invention are by no means limited to the above-mentioned specific dose forms.

The preparations according to the present invention may comprise a wide variety of known bases or vehicles according to the desired dose form as long as the effects of the present invention are not impaired. Such bases or vehicles include oils, e.g., avocado oil, tubaki oil (camellia oil), evening primrose oil, Turtle oil, Macadamia nut oil, corn oil, mink oil, olive oil, rape oil, egg yolk oil, sesame oil, persic oil (apricot kernel oil), wheat germ oil, sasanqua oil, castor oil, linseed oil, safflower oil, cotton seed oil, perilla oil, soybean oil, peanut oil, tea seed oil, kaya (*Torreya nucifera*) oil, rice bran oil, Chinese tung oil, Japanese tung oil, jojoba oil, germ oil, triglycerides (e.g., glycerol trioctanoate and glycerol triisopalmitate); fats, such as cacao fat, coconut oil, horse fat, hardened coconut oil, palm oil, beef tallow, mutton tallow, hardened beef tallow, palm kernel oil, lard, beef bone fat, haze (*Rhus succedancea* L.) kernel oil, hardened oil, beef foot oil, Japan wax, and hardened castor oil; waxes, such as molasses, candelilla wax, cotton wax, carnauba wax, bayberry wax, cera ibota, whale wax, montan wax, rice bran wax, lanolin, kapok wax, lanolin acetate, liquid lanolin, sugar cane wax, lanolin fatty acid isopropyl ester, hexyl laurate, hydrogenated lanolin, jojoba wax, hard lanolin, Shellac wax, polyoxyethylene (hereinafter abbreviated as POE) lanolin alcohol ether, POE lanolin alcohol acetate, POE cholesterol ether, polyethylene glycol lanolin fatty acid ester, and POE hydrogenated lanolin alcohol ether; hydrocarbon oils, such as liquid paraffin, ozokerite, squalene, pristane, paraffin, ceresin, vaseline, and microcrystalline wax; higher fatty acids, e.g., lauric acid, myristic acid, palmitic acid, stearic acid, behenic acid, oleic acid, 12-hydroxystearic acid, undecylenic acid, Tall oil, isostearic acid, linoleic acid, linolenic acid, eicosapentaenoic acid (EPA), and docosahexaenoic acid (DHA); higher alcohols including straight-chain alcohols, such as lauryl alcohol, cetyl alcohol, stearyl alcohol, behenyl alcohol, myristyl alcohol, oleyl alcohol, and cetostearyl alcohol, and branched alcohols, such as monostearyl glycerol ether (batyl alcohol), 2-decyltetradecinol, lanolin alcohol, cholesterol, phytosterol, hexyldodecanol, isostearyl alcohol, and octyldodecanol; synthetic ester oils, such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, diisostearyl malate, glycerol di-2-heptylundecanoate, trimethylolpropane tri-2-ethylhexylate, trimethylolpropane triisostearate, pentaerythritol tetra-2-ethylhexylate, glycerol tri-2-ethylhexylate, trimethylolpropane triisostearate, cetyl 2-ethylhexylate, 2-ethylhexyl palmitate, glycerol trimyristate, glycerol tri-2-heptylundecanoate, castor oil fatty acid methyl ester, oleic acid oil, cetearyl alcohol, acetglyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate; silicone derivatives including chain polysiloxanes, such as dimethyl polysiloxane, methylphenyl polysiloxane, and methylhydrogen polysiloxane, cyclic polysiloxanes, such as decamethyl polysiloxane, dodecamethyl polysiloxane, and tetramethyltetrahydrogen polysiloxane, silicone resins forming a three-dimensional network structure, and silicone rubber; anionic surface active agents, such as soap base, fatty acid soaps (e.g., sodium laurate or sodium palmitate), higher alkylsulfates (e.g., sodium lauryl sulfate and potassium lauryl sulfate), alkyl ether sulfates (e.g., POE triethanolamine lauryl sulfate and POE sodium lauryl sulfate), N-acylsarcosine (e.g., sodium lauroylsarcosine), higher fatty acid amide sulfonates (e.g., sodium N-myristoyl-N-methyltaurine, sodium coconut-oil fatty acid-methyltaurine, and sodium laurylmethyltaurin), phosphoric ester salts (e.g., sodium POE oleyl ether phosphate and POE stearyl ether phosphoric acid), sulfosuccinates (e.g., sodium di-2-ethylhexylsulfosuccinate, sodium monolauroylmonoethanolamide polyoxyethylene sulfosuccinate, and sodium lauryl polypropylene glycol sulfosuccinate), alkylbenzenesulfonates (e.g., sodium linear dodecylbenzenesulfonate, triethanolamine linear dodecylbenzenesulfonate, linear dodecylbenzenesulfonic acid), N-acylglutamates (e.g., sodium N-lauroylglutamate, disodium N-stearoylglutamate, and monosodium N-myristoyl-L-glutamate), higher fatty acid ester sulfates (e.g., sodium glycerol hardened coconut oil fatty acid sulfate), sulfated oils (e.g., Turkey red oil), POE alkyl ether carboxylic acids, POE alkyl allyl ether carboxylates, α-olefinsulfonates, higher fatty acid ester sulfonates, secondary alcohol sulfates, higher fatty acid alkylolamidosulfates, sodium lauroyl monoethanolamidosuccinate, ditriethanolamine N-palmitoylaspartate, and casein sodium; cationic surface active agents, such as alkyltrimethylammonium salts (e.g., stearyltrimethylammonium chloride and lauryltrimethylammonium chloride), distearyldimethylammonium chloride, alkylpyridinium salts (e.g., poly(N,N'-dimethyl-3,5-methylenepiperidinium) chloride and cetylpyridinium chloride), alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride; amphoteric surface active agents, such as imidazoline type amphoteric surface active agents (e.g., sodium 2-undecyl-N,N,N-(hydroxyethylcarboxymethyl)-2-imidazoline and 2-cocoyl-2-imidazolinium hydroxide-1-carboxyethyloxy disodium), and betaine type amphoteric surface active agents (e.g., 2-heptadecyl-N-carboxymethyl-N-hydroxyethylimidazolinium betaine, lauryldimethylaminoacetic acid betaine, alkylbetaines, amidobetaines, and sulfobetaines; lipophilic nonionic surface active agents, such as sorbitan fatty acid esters (e.g., sorbitan mono-oleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate), glycerol fatty acid esters (e.g., glycerol mono-cotton seed oil fatty acid ester, glycerol monoerucate, glycerol sesquioleate, glycerol monostearate, glycerol α,α'-oleate pyroglutamate, and glycerol monostearate malate), propylene glycol fatty acid esters (e.g., propylene glycol monostearate), hardened castor oil derivatives, glycerol alkyl ethers, and polyoxyethylene-methyl polysiloxane copolymers; hydrophilic nonionic surface active agents, such as POE sorbitan fatty acid esters (e.g., POE sorbitan mono-oleate, POE sorbitan monostearate and POE sorbitan tetraoleate), POE sorbitol fatty acid esters (e.g., POE sorbitol monolaurate, POE sorbitol mono-oleate, POE sorbitol pentaoleate, and POE sorbitol monostearate), POE glycerol fatty acid esters (e.g., POE glycerol monostearate, POE glycerol monoisostearate, and POE glycerol triisostearate), POE fatty acid esters (e.g., POE mono-oleate, POE distearate, POE monodioleate, and ethylene glycol distearate), POE alkyl ethers (e.g., POE lauryl ether, POE oleyl ether, POE stearyl ether, POE behenyl ether, POE 2-octyldodecyl ether, and POE cholestanol ether), POE alkyl phenyl ethers (e.g., POE octyl phenyl ether, POE nonyl phenyl ether, and POE dinonyl phenyl ether), polyoxyethylene polypropylene glycol ether (e.g., Pluronic), POE-POP alkyl ethers (e.g., POE-POP cetyl ether, POE-POP 2-decyltetradecyl ether, POE-POP monobutyl ether, POE-POP hydrogenated lanolin, and POE-POP glycerol ether), tetra POE-tetra POP ethylenediamine condensates (e.g., Tetronic), POE castor oil or hardened castor oil derivatives (e.g., POE castor oil, POE hardened castor oil, POE hardened castor oil monoisostearate, POE hardened castor oil triisostearate, POE hardened-castor oil monopyroglutamate monoisostearate, and POE hardened castor oil maleate), POE molasses lanolin derivatives (e.g., POE sorbitol molasses), alkanolamides (e.g., coconut oil fatty acid diethanolamide, lauric monoethanolamide, and fatty acid isopropanolamide), POE propylene glycol fatty acid esters, POE alkylamines, POE fatty acid amides, sucrose fatty acid esters, POE nonylphenyl formamide condensate, alkylethoxydimethylamine oxides, and trioleyl phosphate; antiseptics such as methyl p-hydroxybenzoate, ethyl p-hydroxybenzoate, and butyl p-hydroxybenzoate; masking agents, such as disodium edetate and EDTA; naturally occurring water-soluble high polymers including vegetable high polymers, such as gum arabic, tragacanth, galactan, guar gum, carob gum, karaya gum, carrageenan, pectin, agar, quince seeds, algae colloid (brown algae extract), starch (rice, corn, potato or wheat), and glycyrrhizic acid, microorganism high polymers, such as xantham gum, dextran, succinoglucan, and pullulan, and animal high polymers, such as collagen, casein, albumin, and gelatin; semisynthetic water-soluble high polymers, such as starch high polymers (e.g., carboxymethyl starch and methylhydroxypropyl starch), cellulose high polymers (e.g., methyl cellulose, nitrocellulose, ethyl cellulose, methylhydroxypropyl cellulose, hydroxyethyl cellulose, sodium cellulose sulfate, hydroxypropyl cellulose, carboxymethyl cellulose (CMC) sodium, microcrystalline cellulose, and powdered cellulose), and alginic acid high polymers (e.g., sodium alginate and propylene glycol alginate); synthetic water-soluble high polymers, such as vinyl polymers (e.g., polyvinyl alcohol, polyvinyl methyl ether, polyvinylpyrrolidone, carboxyvinyl polymer (Carbopol), and alkyl-modified carboxyvinyl polymers), polyoxyethylene high polymers (e.g., polyethylene glycol 2000, 4000 or 6000), polyoxyethylene-polyoxypropylene copolymers, acrylic polymers (e.g., sodium polyacrylate, polyethyl acrylate, and polyacrylamide), polyethylene-imine, and cationic polymers; inorganic water-soluble high polymers, such as bentonite, magnesium aluminum silicate, laponite, hectorite, and silicic anhydride; thickeners, such as gum arabic, carrageenan, karaya gum, tragacanth, carob gum, quince seeds, casein, dextrin, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust beam gum, guar gum, tamarind gum, cellulose dialkyldimethylammonium sulfate, xantham gum, aluminum magnesium silicate, bentonite, and hectorite; powder components including inorganic powders, such as talc, kaolin, mica, sericite, commonmica, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (calcined gypsum), calcium phosphate, fluorapatite, hydroxyapatite, ceramic powder, metal soaps (e.g., zinc myristate, calcium palmitate and aluminum stearate), and boron nitride, and organic powders, such as polyamide resin powder (nylon powder), polyethylene powder, polymethyl methacrylate powder, polystyrene powder, styrene-acrylic acid copolymer resin powder, benzoguanamine resin powder, polytetrafluoroethylene powder, and cellulose powder; colorants, such as inorganic white pigments (e.g., titanium dioxide and zinc oxide), inorganic red pigments (e.g., iron oxide and iron titanate), inorganic brown pigments (e.g., γ-iron oxide), inorganic yellow pigments (e.g., yellow iron oxide and ocher), inorganic black pigments (e.g., black iron oxide, carbon black, and titanium oxide of low order), inorganic purple pigments (e.g., mango violet and cobalt violet), inorganic green pigments (e.g., chromium oxide, chromium hydroxide, and cobalt titanate), inorganic blue pigments (e.g., ultramarine and Prussian blue), pearlescent pigments (e.g., titanium oxide-coated mica, titanium oxide-coated bismuth oxychloride, titanium oxide-coated talc, colored titanium oxide-coated mica, bismuth oxychloride, and fish scale guanine), metal powder pigments (e.g., aluminum powder and copper powder), organic pigments (e.g., Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404), zirconium, barium or aluminum lake organic pigments (e.g., Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1), natural dyes (e.g., chlorophyll and β-carotene), Titan Yellow, carthamin, and safflower; perfumes; water; alcohols; and the like.

The present invention will now be illustrated in greater detail with reference to Test Examples and Formulation Examples, but it should be understood that the present invention is not construed as being limited thereto.

TEST EXAMPLE 1

Inhibitory Effect of Compound (I) on Collagen Cross-linking

Collagen was extracted from human placenta by pepsin treatment and purified by salting out (Nishihara T. and Miyata T., *Collagen Synposium*, Vol. 3,pp. 66–93 (1962)). The purity of the thus prepared collagen was 94% as measured by electrophoresis (Hayahi T. and Nagai Y., *J. Biochem.*, Vol. 86,No. 2,pp. 453–459 (1962)). The collagen (final concentration: 1 mg/ml) was kept in a phosphate buffered saline at pH 7.4 and 37° C. to form collagen fiber and irradiated with UV light of 7.0 J/cm² (TOSHIBA FL30S•BLB lamp, UV-A region, peak: 365 nm) at a UV-A intensity of 1.4 mW/cm² for 90 minutes in the absence (control) or presence of 2-aminoethylthiosulfonic acid having a varied concentration as shown in Table 1 below (Run Nos. 1 to 8).

The collagen after UV irradiation was analyzed by electrophoresis and with a densitometer (Fluorescent Densitometer F-808, manufactured by Cosmo K.K.) to obtain the degree of collagen cross-linking induced by the UV irradiation. The percent inhibition of collagen cross-linking by addition of 2-aminoethylthiosulfonic acid was calculated from equation:

Precent inhibition (%) = 100 −

[(Degree of cross-linking of collagen in irradiated sample) −

(Degree of cross-linking of collagen in non-irradiated sample)]/

[(Degree of cross-linking of collagen in irradiated control) −

(Degree of cross-linking of collagen in non-irradiated control)] × 100

(Control: phosphate buffered saline)

The results obtained are shown in Table 1.

TABLE 1

| Run No. | Concn. of 2-Amino-ethylthiosulfonic Acid (wt %) | Percent Inhibition (%) |
|---|---|---|
| Control | none (0.01M phosphate buffered saline) | 0 |
| 1 | 5.0 | 79 |
| 2 | 1.0 | 80 |
| 3 | 0.5 | 78 |
| 4 | 0.1 | 70 |
| 5 | 0.05 | 62 |
| 6 | 0.01 | 54 |
| 7 | 0.001 | 48 |
| 8 | 0.0001 | 28 |

As is apparent from the results in Table 1, collagen cross-linking intimately relating to cutaneous aging is inhibited by the existence of 2-aminoethylthiosulfonic acid as described before. That is, it has been proved that 2-aminoethylthiosulfonic acid is highly useful as an active ingredient of the anti-aging preparation, collagen cross-linking inhibitory preparation and anti-UV preparation according to the present invention.

It has been revealed from the results of Run Nos. 6 and 7 that the 2-aminoethylthiosulfonic acid should be present in the above test system at a concentration of 0.01% by weight or higher in order to surely achieve 50% or more inhibition on collagen cross-linking.

As has been ascertained from the results of Run Nos. 7 and 8, if the concentration of 2-aminoethylthiosulfonic acid in the test system is less than 0.001% by weight, it is difficult to effectively inhibit collagen cross-linking. On the other hand, the result of Run No. 1 shows that concentration of 2-aminoethylthiosulfonic acid exceeding 1.0% by weight does not bring about any further improvement.

TEST EXAMPLE 2

Synergism of Combined Use of UV Absorber

2-Aminoethylthiosulfonic acid was used in combination with sodium 2-hydroxy-4-methoxybenzophenone-5-sulfate as an UV-A absorber, and the synergistic effect on UV-induced collagen cross-linking was examined in the same manner as in Test Example 1. The results obtained are shown in Table 2.

TABLE 2

| Run No. | Concn. of 2-Aminoethylthiosulfonic Acid (wt %) | Concn. of Sodium 2-Hydroxy-4-methoxy-benzophenone-5-sulfonate (wt %) | Percent Inhibition (%) |
|---|---|---|---|
| 9 | 0.1 | 30.0 | 80 |
| 10 | 0.1 | 20.0 | 85 |
| 11 | 0.1 | 10.0 | 87 |
| 12 | 0.1 | 5.0 | 85 |
| 13 | 0.1 | 1.0 | 80 |
| 14 | 0.1 | 0.5 | 79 |
| 15 | 0.1 | 0.1 | 78 |
| 16 | 0.1 | 0.05 | 74 |
| 17 | 0.1 | 0.01 | 71 |
| 18 | 0.1 | 0.005 | 70 |
| Control 2 | 0.1 | 0 | 70 |
| Control | 0 | 0 | 0 |

TABLE 2-continued

| Run No. | Concn. of 2-Aminoethylthio-sulfonic Acid (wt %) | Concn. of Sodium 2-Hydroxy-4-methoxy-benzophenone-5-sulfonate (wt %) | Percent Inhibition (%) |
|---|---|---|---|
| 3 | | | |

As is seen from Table 2, the test systems containing a combination of 2-aminoethylthiosulfonic acid and sodium 2-hydroxy-4-methoxybenzophenone-5-sulfonate as a UV-A absorber exhibit synergism in inhibition on collagen cross-linking. That is, it has been proved that a combined use of 2-aminoethylthiosulfonic acid and sodium 2-hydroxy-4-methoxybenzophenone-5-sulfonate as active ingredients is an extremely useful prescription for the anti-aging preparation, collagen cross-linking inhibitory preparation and anti-UV preparation according to the present invention.

It is also seen from the results of Run Nos. 17 and 18 that, in the test system containing 0.1% by weight of aminoethylthiosulfonic acid, the sodium 2-hydroxy-4-methoxybenzophenone-5-sulfonate should be added in a concentration of from 0.1 to 20.0% by weight based on the total test system so as to produce the synergistic effect. That is, if the concentration of sodium 2-hydroxy-4-methoxybenzophenone-5-sulfonate is less than 0.01% by weight in that system, no substantial synergism is obtained (Run Nos. 17 and 18), and even if the concentration exceeds 30% by weight, no further improvement in synergism results (Run Nos. 9 and 10).

While the above test runs were conducted using sodium 2-hydroxy-4-methoxybenzophenone-5-sulfonate as a sole example of UV absorbers, it would be safe to assume that the synergism shown in Table 2 owes to the fact that this particular UV absorber inhibits mainly UV-A from reaching collagen. It is obvious therefore that similar synergism would be displayed where the preparations of the present invention to contain other UV absorbers, especially UV-A absorbers because collagen of a living body exists predominantly in the dermis, not in the epidermis.

TEST EXAMPLE 3

Synergism of Combined Use of Active Ingredients

2-Aminoethylthiosulfonic acid was used in combination with the other aminoethyl compound (I), i.e., 2-aminoethylsulfinic acid, and sodium 2-hydroxy-4-methoxybenzophenone-5-sulfate as a UV-A absorber and/or octyl methoxycinnamate as a UV-B absorber, and the synergistic effect on UV-induced collagen cross-linking was examined in the same manner as in Test Example 1. The results obtained are shown in Table 3.

TABLE 3

| Run No. | Concentration of Active Ingredient (wt %) | | | | Percent Inhibition (%) |
|---|---|---|---|---|---|
| | 2-Aminoethyl-thio-sulfonic Acid | 2-Amino-ethyl-sulfinic Acid | Sodium 2-Hydroxy-4-methoxy-benzophenone-5-sulfonate | Octyl Methoxy-cinnamate | |
| 19 | 0.05 | 0.05 | 0 | 0 | 72 |
| 20 | 0.05 | 0.05 | 1 | 0 | 88 |
| 21 | 0.05 | 0.05 | 0 | 1 | 78 |
| 22 | 0.05 | 0.05 | 1 | 1 | 92 |
| Control 4 | 0.1 | 0 | 0 | 0 | 68 |
| Control 5 | 0 | 0.1 | 0 | 0 | 65 |
| Control 6 | 0 | 0 | 1 | 0 | 51 |
| Control 7 | 0 | 0 | 0 | 1 | 40 |
| Control 8 | 0 | 0 | 0 | 0 | 0 |

Comparing Run No. 19 with Controls 4 and 5, it is obvious that a combination of 2-aminoethylthiosulfonic acid and 2-aminoethylsulfinic acid tends to exhibit superior effects as compared with the isolated use of each.

As is shown in Run No. 20 very high inhibitory activity on collagen cross-linking appears when a combination of two aminoethyl compounds (I) is further combined with sodium 2-hydroxy-4-methoxybenzophenone-5-sulfonate.

As is shown in Run No. 21 high inhibitory activity on collagen cross-linking also appears when a combination of two aminoethyl compounds (I) is further combined with octyl methoxycinnamate.

As is shown in Run No. 22 inhibition of collagen cross-linking is most effectively exhibited when a combination of two aminoethyl compounds (I) is further combined with the two UV absorbers.

Control 5 proves that 2-aminoethylsulfinic acid when used alone exhibits substantially equal inhibitory activity on collagen cross-linking to that exhibited in using 2-aminoethylthiosulfonic acid alone (Test Example 1).

Comparison between Controls 6 and 7 (or Run Nos. 20 and 21) implies that a UV-A absorber is more effective than a UV-B absorber when incorporated into the preparation of the present invention. That is, although octyl methoxycinnamate (UV-B absorber) has a higher peak of UV absorption than sodium 2-hydroxy-4-methoxybenzophenone-5-sulfonate (UV-A absorber), the test results suggest that the latter UV absorber tends to produce higher activity when used alone or higher synergism when used in combination with the aminoethyl compound (I).

Formulation examples of the preparation according to the present invention are shown below. All the percents are by weight. All the preparations prepared exhibited excellent inhibitory effects on cutaneous aging, excellent inhibitory effects on collagen cross-linking and excellent anti-UV effects.

FORMULATION EXAMPLE 1

| Clear Lotion | |
|---|---|
| (1) 2-Aminoethylthiosulfonic acid | 0.05% |
| (2) Sodium hydroxy-4-methoxybenzophenone-5-sulfonate | 0.1% |

-continued

| Clear Lotion | |
|---|---|
| (3) Tocopherol acetate | 0.01% |
| (4) Glycerin | 4.0% |
| (5) 1,3-Butylene glycol | 4.0% |
| (6) Ethanol | 8.0% |
| (7) Polyoxyethylene (60) hardened castor oil | 0.5% |
| (8) Methyl p-hydroxybenzoate | 0.2% |
| (9) Citric acid | 0.05% |
| (10) Sodium citrate | 0.1% |
| (11) Perfume | 0.05% |
| (12) Purified water | balance |

2-Aminoethylthiosulfonic acid (1), sodium hydroxy-4-methoxybenzophenone-5-sulfonate (2), citric acid (9), sodium citrate (10), glycerin (4), and 1,3-butylene glycol (5) were dissolved in purified water (12). Separately, polyoxyethylene (60) hardened castor oil (7), tocopherol acetate (3), perfume (11), and methyl p-hydroxybenzoate (8) were dissolved in ethanol (6), and the ethanolic solution was added to the above prepared aqueous solution and dissolved therein, followed by filtration to give a clear lotion.

FORMULATION EXAMPLE 2

| Cream | |
|---|---|
| (1) Cetostearyl alcohol | 3.5% |
| (2) Squalane | 40.0% |
| (3) Molasses | 3.0% |
| (4) Hydrogenated lanolin | 5.0% |
| (5) Ethyl p-hydroxybenzoate | 0.3% |
| (6) Polyoxyethylene (20) sorbitan monopalmitate | 2.0% |
| (7) Glycerol monostearate | 2.0% |
| (8) Sodium N-stearoylglutamate | 0.5% |
| (9) 4-Methoxy-4'-t-butyldibenzoylmethane | 1.0% |
| (10) Octyl methoxycinnamate | 10.0% |
| (11) Retinol acetate | 2.0% |
| (12) Evening primrose oil | 0.05% |
| (13) Perfume | 0.03% |
| (14) 2-Aminoethylsulfinic acid | 0.1% |
| (15) 1,3-Butylene glycol | 5.0% |
| (16) Polyethylene glycol 1500 | 5.0% |
| (17) Purified water | balance |

Cetostearyl alcohol (1), squalane (2), molasses (3), hydrogenated lanolin (4), ethyl p-hydroxybenzoate (5), polyoxyethylene (20) sorbitan monopalmitate (6), glycerol monostearate (7), sodium N-stearoylglutamate (8), 4-methoxy-4'-t-butyldibenzoylmethane (9), octyl methoxycinnamate (10), retinol acetate (11), evening primrose oil (12), and perfume (13) were melted by heating (oily phase). In purified water (17) were dissolved 2-aminoethylsulfinic acid (14), 1,3-butylene glycol (15), and polyethylene glycol 1500 (16), and the aqueous solution was kept at 70° C. (aqueous phase). The oily phase was added to the aqueous phase while stirring, and the mixture was finely divided in a homo-mixer and rapidly cooled with stirring to obtain cream.

FORMULATION EXAMPLE 3

| Milky Lotion | |
|---|---|
| (1) 2-Ethylhexyl p-dimethylaminobenzoate | 0.1% |
| (2) Mono-2-ethylhexyl di-p-methoxycinnamate | 0.2% |
| (3) Stearic acid | 1.5% |

-continued

| Milky Lotion | |
|---|---|
| (4) Cetyl alcohol | 0.5% |
| (5) Molasses | 2.0% |
| (6) Polyoxyethylene (10) mono-oleate | 2.0% |
| (7) L-Arginine | 0.3% |
| (8) Sodium L-glutamate | 0.02% |
| (9) PCA-Na | 0.05% |
| (10) 2-Aminoethylthiosulfonic acid | 0.2% |
| (11) 2-Aminoethylsulfinic acid | 0.01% |
| (12) Propylene glycol | 5.0% |
| (13) Glycerin | 3.0% |
| (14) Ethanol | 3.0% |
| (15) Ethyl p-hydroxybenzoate | 0.3% |
| (16) Perfume | 0.03% |
| (17) carboxyvinyl polymer | 0.12% |
| (18) Purified water | balance |

2-Aminoethylthiosulfonic acid (10), 2-aminoethylsulfinic acid (11), L-arginine (7), sodium L-glutamate (8), PCA-Na (9), propylene glycol (12), glycerin (13), ethanol (14), and carboxyvinyl polymer (17) were added to purified water (18) and dissolved by heating, and the resulting solution was kept at 70° C. (aqueous phase). Other components were mixed, melted by heating, and maintained at 70° C. (oily phase). The oily phase was added to the aqueous phase. The mixture was preliminarily emulsified and then uniformly emulsified in a homo-mixer, followed by rapidly cooling while stirring to obtain a milky lotion.

FORMULATION EXAMPLE 4

| Mask Mousse | |
|---|---|
| (1) 2-Aminoethylthiosulfonic acid | 1.0% |
| (2) 2-Hydroxy-4-methoxybenzophenone | 0.1% |
| (3) Stearic acid | 1.0% |
| (4) Behenic acid | 1.0% |
| (5) Self-emulsifiable glycerol monostearate | 1.5% |
| (6) Polyoxyethylene (5) glycerol monostearate | 2.5% |
| (7) Batyl alcohol | 1.5% |
| (8) Perfume | 0.05% |
| (9) Glycerin | 5.0% |
| (10) 1,3-Butylene glycol | 5.0% |
| (11) Polyethylene glycol 1500 | 3.0% |
| (12) Methyl p-hydroxybenzoate | 0.1% |
| (13) Potassium hydroxide | 0.15% |
| (14) Purified water | balance |
| (15) Liquefied petroleum gas | 6.0% |
| (16) Dimethyl ether | 2.0% |

2-Aminoethylthiosulfonic acid (1), glycerin (9), 1,3-butylene glycol (10), polyethylene glycol 1500 (11), methyl p-hydroxybenzoate (12), and potassium hydroxide (13) were added to purified water (14) and dissolved therein by heating at 70° C. (aqueous phase). Other components were mixed, melted by heating, and maintained at 70° C. (oily phase). The oily phase was added to the aqueous phase, and the mixture was uniformly mixed, cooled, and charged in a container. Finally, liquefied gas and dimethyl ether were added thereto as atomizing agent to obtain a mask mousse.

FORMULATION EXAMPLE 5

| Ointment | |
|---|---|
| (1) 2-Aminoethylthiosulfonic acid | 0.1% |
| (2) 2-Aminoethylsulfinic acid | 1.0% |

| Ointment | |
|---|---|
| (3) Sodium 2-hydroxy-4-methoxybenzophenone-5-sulfonate | 0.5% |
| (4) Octyl p-dimethylaminobenzoate | 4.0% |
| (5) Butylmethoxybenzoylmethane | 1.0% |
| (6) Tocopherol acetate | 0.5% |
| (7) Retinol palmitate | 1.0% |
| (8) Stearyl alcohol | 18.0% |
| (9) Japan wax | 20.0% |
| (10) Polyoxyethylene (10) mono-oleate | 0.25% |
| (11) Glycerol monostearate | 0.3% |
| (12) Vaseline | 32.0% |
| (13) Purified water | balance |

2-Aminoethylthiosulfonic acid (1), 2-aminoethylsulfinic acid (2), and sodium 2-hydroxy-4-methoxybenzophenone-5-sulfonate were dissolved in purified water (13) and kept at 70° C. (aqueous phase). Other components were mixed and melted at 70° C. (oily phase). The oily phase was added to the aqueous phase, and the mixture was uniformly emulsified in a homo-mixer and cooled to obtain an ointment.

FORMULATION EXAMPLE 6

| Sun-screening Milky Lotion | |
|---|---|
| (1) Stearic acid | 2.0% |
| (2) Cetyl alcohol | 0.5% |
| (3) Liquid paraffin | 10.0% |
| (4) Polyoxyethylene (10) oleate | 1.0% |
| (5) Sorbitan trioleate | 1.0% |
| (6) 2-Hydroxy-4-methoxybenzophenone | 3.0% |
| (7) 2,2'-Hydroxy-5-methylphenylbenzotriazole | 1.0% |
| (8) Glycerol mono-2-ethylhexanoyl di-p-methoxycinnamate | 1.0% |
| (9) Octyl methoxycinnamate | 7.0% |
| (10) Ethyl p-hydroxybenzoate | 0.3% |
| (11) Perfume | 0.2% |
| (12) 1,3-Butylene glycol | 5.0% |
| (13) Dipropylene glycol | 3.0% |
| (14) 2-Aminoethylthiosulfonic acid | 0.5% |
| (15) 2-Aminoethylsulfinic acid | 1.0% |
| (16) Carboxyvinyl polymer | 0.15% |
| (17) Trisodium edetate | 0.05% |
| (18) Triethanolamine | 0.4% |
| (19) Silica | 2.0% |
| (20) Talc | 2.0% |
| (21) Titanium oxide | 3.0% |
| (22) Zinc oxide | 3.0% |
| (23) Purified water | balance |

Components from 1,3-butylene glycol (12) to triethanolamine (18) were dissolved in purified water (23). Components from silica (19) to zinc oxide (22) were dispersed therein, and the dispersion was kept at 70° C. (aqueous phase). Separately, components from stearic acid (1) to perfume (11) were mixed and melted by heating, and the mixture was added to the aqueous phase. The mixture was uniformly emulsified in a homo-mixer and rapidly cooled with stirring to obtain a sun-screening milky lotion.

FORMULATION EXAMPLE 7

| Sun-screening Cream | |
|---|---|
| (1) Decamethylcyclopentasiloxane | 30.0% |
| (2) Liquid paraffin | 5.0% |
| (3) Polyoxyalkylene-modified organopolysiloxane | 1.5% |

| Sun-screening Cream | |
|---|---|
| (4) Distearyldimethylammonium chloride | 0.6% |
| (5) Octyl methoxycinnamate | 12.0% |
| (6) 4-t-Butyl-4'-methoxybenzoylmethane | 0.1% |
| (7) Glycerol mono-2-ethylhexanoyl-di-p-methoxycinnamate | 0.1% |
| (8) Ethyl p-hydroxybenzoate | 0.2% |
| (9) Perfume | 0.3% |
| (10) Titanium oxide | 10.0% |
| (11) Zinc oxide | 5.0% |
| (12) Talc | 2.0% |
| (13) Glycerin | 5.0% |
| (14) 2-Aminoethylthiosulfonic acid | 0.5% |
| (15) 2-Aminoethylsulfinic acid | 0.1% |
| (16) Magnesium aluminum silicate | 1.0% |
| (17) Purified water | balance |

Components from decamethylcyclopentasiloxane (1) to perfume (9) were mixed and melted at 70° C. (oily phase). To the oily phase were added components from titanium oxide (10) to 2-aminoethylsulfinic acid (15), and the mixture was dispersed in a dispersion mixer. Separately, components from glycerin (13) to magnesium aluminum silicate (16) were dissolved or dispersed in purified water (17) and kept at 70° C. (aqueous phase). The aqueous phase was slowly added to the oily phase while stirring in a dispersion mixer, and the mixture was thoroughly stirred and rapidly cooled to obtain sun-screening cream.

As has been fully described, the present invention provides an anti-aging preparation for cutaneous application which inhibits cutaneous aging, a collagen cross-linking inhibitory preparation for cutaneous application which inhibits collagen cross-linking occurring predominantly in the dermis to maintain skin elasticity and to suppress wrinkles or sagging, and an anti-UV preparation for cutaneous application which protects the skin from harmful effects of excessive exposure to ultraviolet rays of sunlight.

While the invention has been described in detail and with reference to specific examples thereof, it will be apparent to one skilled in the art that various changes and modifications can be made therein without departing from the spirit and scope thereof.

What is claimed is:

1. A method of inhibiting cutaneous aging, said method comprising applying an effective amount of an anti-aging composition to skin, the anti-aging composition comprising at least one aminoethyl compound represented by formula (I):

$$NH_2CH_2CH_2X \qquad (I);$$

and at least one ultraviolet protective agent, wherein X represents —$SO_2$ or —$SO_2SH$.

2. A method of inhibiting collagen cross-linking, said method comprising applying an effective amount of an anti-aging composition to skin, the anti-aging composition comprising at least one aminoethyl compound represented by formula (I):

$$NH_2CH_2CH_2X \qquad (I);$$

and at least one ultraviolet protective agent, wherein X represents —$SO2$ or —$SO_2SH$.

3. A method of protecting skin from harmful effects caused by excessive exposure to ultraviolet light, said method comprising applying an effective amount of an anti-aging composition to skin, the anti-aging composition comprising at least one aminoethyl compound represented by formula (I):

$$NH_2CH_2CH_2X \quad (I);$$

and at least one ultraviolet protective agent, wherein X represents $—SO_2$ or $—SO_2SH$.

4. A method according to claim 1, wherein the ultraviolet protective agent comprises at least one long-wavelength ultraviolet protective agent.

5. A method according to claim 4, wherein the long-wavelength ultraviolet protective agent is at least one member selected from the group consisting of 4-methoxy-4'-t-butyldibenzoylmethane, 2-hydroxy-4-methoxybenzophenone, a 2-hydroxy-4-methoxybenzophenone-5-sulfonic acid salts.

6. A method according to claim 1, wherein the aminoethyl compound is present in the composition in a concentration of from 0.001 to 1.0% by weight.

7. A method according to claim 1, wherein the aminoethyl compound is present in the composition in a concentration of from 0.1 to 0.5% by weight.

8. A method according to claim 1, wherein the ultraviolet protective agent is present in the composition in a concentration of from 0.01 to 30% by weight.

9. A method according to claim 1, wherein the ultraviolet protective agent is present in the composition in a concentration of from 0.1 to 20% by weight.

10. A method according to claim 2, wherein the ultraviolet protective agent comprises at least one long-wavelength ultraviolet protective agent.

11. A method according to claim 10, wherein the long-wavelength ultraviolet protective agent is at least one member selected from the group consisting of 4-methoxy-4'-t-butyldibenzoylmethane, 2-hydroxy-4-methoxybenzophenone, a 2-hydroxy-4-methoxybenzophenone-5-sulfonic acid salts.

12. A method according to claim 2, wherein the aminoethyl compound is present in the composition in a concentration of from 0.001 to 1.0% by weight.

13. A method according to claim 2, wherein the aminoethyl compound is present in the composition in a concentration of from 0.1 to 0.5% by weight.

14. A method according to claim 2, wherein the ultraviolet protective agent is present in the composition in a concentration of from 0.01 to 30% by weight.

15. A method according to claim 2, wherein the ultraviolet protective agent is present in the composition in a concentration of from 0.1 to 20% by weight.

16. A method according to claim 3, wherein the ultraviolet protective agent comprises at least one long-wavelength ultraviolet protective agent.

17. A method according to claim 16, wherein the long-wavelength ultraviolet protective agent is at least one member selected from the group consisting of 4-methoxy-4'-t-butyldibenzoylmethane, 2-hydroxy-4-methoxybenzophenone, a 2-hydroxy-4-methoxybenzophenone-5-sulfonic acid salts.

18. A method according to claim 3, wherein the aminoethyl compound is present in the composition in a concentration of from 0.001 to 1.0% by weight.

19. A method according to claim 3, wherein the aminoethyl compound is present in the composition in a concentration of from 0.1 to 0.5% by weight.

20. A method according to claim 3, wherein the ultraviolet protective agent is present in the composition in a concentration of from 0.01 to 30% by weight.

21. A method according to claim 3, wherein the ultraviolet protective agent is present in the composition in a concentration of from 0.1 to 20% by weight.

* * * * *